United States Patent
Nakamura et al.

(10) Patent No.: US 10,526,223 B2
(45) Date of Patent: Jan. 7, 2020

(54) METHOD FOR PRODUCING MICROBIOLOGIC AGENT, AND MICROBIOLOGIC AGENT

(71) Applicant: Sumitomo Chemical Company, Limited, Tokyo (JP)

(72) Inventors: Yosuke Nakamura, Osaka (JP); Eiji Nitta, Osaka (JP); Hiroyuki Asako, Osaka (JP); Fumiyoshi Okazaki, Tsu (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/563,696

(22) PCT Filed: Mar. 31, 2016

(86) PCT No.: PCT/JP2016/060772
§ 371 (c)(1),
(2) Date: Oct. 2, 2017

(87) PCT Pub. No.: WO2016/159287
PCT Pub. Date: Oct. 6, 2016

(65) Prior Publication Data
US 2018/0072598 A1    Mar. 15, 2018

(30) Foreign Application Priority Data

Apr. 3, 2015 (JP) ................... 2015-076955

(51) Int. Cl.
| | | |
|---|---|---|
| *C02F 3/34* | (2006.01) | |
| *C12N 1/20* | (2006.01) | |
| *C12N 11/14* | (2006.01) | |
| *C12N 15/10* | (2006.01) | |
| *C12Q 1/6809* | (2018.01) | |
| *C02F 3/30* | (2006.01) | |
| *C12Q 1/689* | (2018.01) | |
| *C02F 101/16* | (2006.01) | |
| *C02F 101/36* | (2006.01) | |

(52) U.S. Cl.
CPC ............... *C02F 3/34* (2013.01); *C02F 3/341* (2013.01); *C12N 1/20* (2013.01); *C12N 11/14* (2013.01); *C12N 15/10* (2013.01); *C12Q 1/6809* (2013.01); *C02F 3/302* (2013.01); *C02F 2101/16* (2013.01); *C02F 2101/36* (2013.01); *C02F 2209/36* (2013.01); *C12Q 1/689* (2013.01)

(58) Field of Classification Search
None
See application file for complete search history.

(56) References Cited

U.S. PATENT DOCUMENTS 5,580,770 A * 12/1996 DeFilippi .................. C02F 3/06
                                                                210/615
2010/0279380 A1   11/2010 Pandey et al.

FOREIGN PATENT DOCUMENTS

| JP | S59-088098 A | | 5/1984 |
|---|---|---|---|
| JP | H6-153989 A | | 6/1994 |
| JP | H9-131178 A | | 5/1997 |
| JP | H9-187272 A | | 7/1997 |
| JP | 2000354484 A | | 12/2000 |
| JP | 2002027976 A | | 1/2002 |
| JP | 2002282826 A | | 10/2002 |
| JP | 2003088355 A | | 3/2003 |
| JP | 2003274937 A | * | 9/2003 |
| JP | 2003274937 A | | 9/2003 |
| JP | 2003334587 A | | 11/2003 |
| JP | 2004008176 A | | 1/2004 |
| JP | 2005007262 A | | 1/2005 |
| JP | 2007268471 A | | 10/2007 |
| JP | 2008142704 A | | 6/2008 |
| JP | 2008212083 A | | 9/2008 |
| JP | 2010531640 A | | 9/2010 |

OTHER PUBLICATIONS

Chen et al. 2013 (Bioremediation potential of soil contaminated with highly substituted polychlorinated dibenzo-p-dioxins and dibenzofurans: Microcosm study and microbial community analysis; Journal of Hazardous Materials 261: 351-361) (Year: 2013).*
Vishnivetskaya et al. 2013 (Microbial Communities Involved in Biological Ammonia Removal for Coal Combustion Wastewaters; Microb Ecol 66:49-59) (Year: 2013).*
Int'l Search Report dated Jun. 28, 2016 in Int'l Application No. PCT/JP2016/060772.
Int'l Preliminary Report on Patentability dated Oct. 12, 2017 in Int'l Application No. PCT/JP2016/060772.
Nakamura et al., "Development of Microorganism Formulation for Bioaugmentation," Sumitomo Kagaku Gijutsushi, vol. 2003-II, pp. 19-25 (Nov. 28, 2003).

(Continued)

*Primary Examiner* — Mary Maille Lyons
(74) *Attorney, Agent, or Firm* — Panitch Schwarze Belisario & Nadel LLP (57) ABSTRACT

A method for producing a microbiologic agent is described. The method includes a step of adding biomass containing a target compound-degrading microorganism and an inorganic microparticle carrier to a medium containing a target compound. The microorganisms included in the biomass are carried on the inorganic microparticles, and the medium is cultured while monitoring an abundance ratio of the target compound-degrading microorganism in microorganisms carried on the inorganic microparticle carrier. After the abundance ratio of the target compound-degrading microorganism reaches a predetermined value, the inorganic microparticle carrier carrying the target compound-degrading microorganism is collected to obtain the microbiologic agent.

3 Claims, 1 Drawing Sheet

Specification includes a Sequence Listing.

(56) References Cited

OTHER PUBLICATIONS

Kraigher, B. et al., "Nitrification activity and community structure of nitrite-oxidizing bacteria in the bioreactors operated with addition of pharmaceuticals," Journal of Hazardous Materials, vol. 188, pp. 78-84 (2011).
Bellucci et al., Chapter Eleven "Ammonia-oxidizing Bacteria in Wastewater," Methods in Enzymology, vol. 496, pp. 269-286 (2011).
Office Action dated Feb. 19, 2019 in JP Application No. 2015-076955 (English Translation).

* cited by examiner

METHOD FOR PRODUCING MICROBIOLOGIC AGENT, AND MICROBIOLOGIC AGENT

CROSS-REFERENCE TO RELATED APPLICATION

This application is a Section 371 of International Application No. PCT/JP2016/060772, filed Mar. 31, 2016, which was published in the Japanese language on Oct. 6, 2016, under International Publication No. WO 2016/159287 A1 and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688101_0054US", creation date of Sep. 27, 2017, and having a size of 1.1 KB. The sequence listing submitted via EFS-Web is part of the specification and is herein incorporated by reference in its entirety.

TECHNICAL FIELD

The present invention relates to a method for producing a microbiologic agent and a microbiologic agent.

BACKGROUND ART

As a method for removing a target compound from drainage in drainage treatment, a method of combustion treatment or a method of biological treatment with a target compound-degrading microorganism or the like is used. As a method for obtaining a target compound-degrading microorganism, a method (a method of isolation culture) involving enrichment culture of microorganisms that degrade target compounds and identification, isolation, and pure culture the degrading microorganism is known. For mixed microorganism systems such as activated sludge, a method called acclimatization (a method of acclimatization) involving acclimating activated sludge to a target compound and increase its degradation capability by providing the target compound at a low concentration as a nutrition source and gradually increasing the concentration is known.

However, there is a problem in the method of isolation culture that it requires a long period of time for isolation of a degrading microorganism, suitable microorganisms are limited to those that can be cultured artificially, and production cost for pure culture is high. Meanwhile, the method of acclimatization allows culturing a degrading microorganism at low cost and in large quantities but there is a problem that a long period of time is required for the acclimatization.

Among other methods for making a target compound degrading microorganism high density, for example, a method for producing a microbiologic agent by making a nitrifying bacterium high density and aggregating microparticle solids and the microorganism into granules, having excellent physical properties is disclosed, as described in Patent Literature 1. This microbiologic agent is useful in effective treatment of drainage since it can be produced efficiently by continuous culture and also stored.

CITATION LIST

Patent Literature

Patent Literature 1: Japanese Unexamined Patent Publication No. 2003-274937

SUMMARY OF INVENTION

Technical Problem

By the method described in Patent Literature 1, it is possible to make nitrifying bacteria high density using the capacity of nitrogen treatment as an indicator, but the kinds and the abundance of the nitrifying bacteria during and after the granulation cannot be, however, known. The same is considered to be true for treatment of a target compound other than nitrogen. With such a method, it is difficult, when using only the degradability of the target compound as an indicator, to predict the proliferation inhibition of the target compound degrading microorganisms due to a too high concentration of the target compound added in the granulation step or the proliferation inhibition, etc. of the target compound degrading microorganism due to the accumulation of degradation intermediates of the target compound since the abundance and the abundance ratio of the target compound-degrading microorganism cannot be known. Meanwhile, due to the progress in recent gene analysis technology, it has become possible to know the kinds and the abundance of microorganism present in a microbial consortium such as activated sludge without isolating microorganisms therefrom. However, the practical use of the technology has so far remained simple measurement and been limited and therefore technological establishment for adapting the gene analysis technology to methods for producing a microbiologic agent has been desired.

In view of the aforementioned circumstances, an object of the present invention is to provide a method for producing stably and efficiently a microbiologic agent carrying a target compound-degrading microorganism at a desired density by monitoring the abundance ratio of the target compound-degrading microorganism. Moreover, an object of the present invention is to provide a microbiologic agent produced by the aforementioned method for production, a method for degrading a compound using the microbiologic agent, and a method for evaluating the microbiologic agent.

Solution to Problem

The present inventors newly established a method for producing a microbiologic agent effectively by monitoring a target compound-degrading microorganism carried by the microbiologic agent based on the gene analysis information from a comprehensive analysis of microorganisms carried on the microbiologic agent during the production, thereby completing the present invention.

Accordingly, the present invention relates to, for example, the following [1] to [6]:

[1] A method for producing a microbiologic agent carrying a target compound-degrading microorganism, comprising a step of adding biomass including the target compound-degrading microorganism and an inorganic microparticle carrier to a medium including a target compound, allowing microorganisms included in the biomass to be carried on the inorganic microparticles, and culturing while monitoring an abundance ratio of the target compound-degrading microorganism in microorganisms carried on the inorganic microparticle carrier; and a step of, after the abundance ratio of the target compound-degrading microorganism reaches a predetermined value, collecting the inorganic microparticle carrier carrying the target compound-degrading microorganism to obtain the microbiologic agent; wherein the abundance ratio of the target compound-degrading microorganism is determined by a method comprising: a step of amplifying a predetermined region of a 16S rRNA gene of microorganisms carried on the inorganic microparticle carrier to obtain an amplified product; and a step of analyzing nucleotide sequence data of the amplified product, dividing the obtained nucleotide sequence data into a plurality of groups based on homologies among the nucleotide sequence data, considering that microorganisms having each group of nucleotide sequence data are of a single kind, determining the kind of the target compound-degrading microorganism based on representative nucleotide sequence data of respective groups, and calculating the abundance ratio of the target compound-degrading microorganism in all microorganisms based on the number of the obtained nucleotide sequence data.

[2] The method for production according to [1], wherein the target compound is (S)-2-(4-chlorophenyl)-3-methylbutanoic acid.

[3] The method for production according to [1], wherein the target compound is ammonia.

[4] A microbiologic agent produced by a method for production according to any one of [1] to [3].

[5] A method for degrading a compound, using a microbiologic agent according to [4].

[6] A method for evaluating a microbiologic agent according to [4], comprising: a step of evaluating the microbiologic agent using the abundance ratio of the target compound-degrading microorganism in the microorganisms included in the microbiologic agent as an indicator; wherein the abundance ratio of the target compound-degrading microorganism is determined by a method comprising: a step of amplifying a predetermined region of a 16S rRNA gene of microorganisms included in the microbiologic agent to obtain an amplified product; and a step of analyzing nucleotide sequence data of the amplified product, dividing the obtained nucleotide sequence data into a plurality of groups based on homologies among the nucleotide sequence data, considering that microorganisms having each group of nucleotide sequence data are of a single kind, determining the kind of the target compound-degrading microorganism based on representative nucleotide sequence data of respective groups, and calculating the abundance ratio of the target compound-degrading microorganism in all microorganisms based on the number of the obtained nucleotide sequence data.

Advantageous Effects of Invention

According to the present invention, a method for producing stably and efficiently a microbiologic agent carrying a target compound-degrading microorganism at a desired density by detecting the kind of microorganisms carried on the microbiologic agent and monitoring the target compound-degrading microorganism based on a calculation of an abundance ratio thereof can be provided. Moreover, the present invention can provide a microbiologic agent produced by the aforementioned method for production, a method for degrading a compound using the microbiologic agent, and a method for evaluating the microbiologic agent.

DESCRIPTION OF EMBODIMENTS

A mode for carrying out the present invention (hereinafter, referred to as the "the present embodiment") is described in detail below. The present invention is not limited to the following embodiment.

<Method for Producing Microbiologic Agent>

A method for producing a microbiologic agent carrying a target compound-degrading microorganism of the present embodiment comprises a step of adding biomass including the target compound-degrading microorganism and an inorganic microparticle carrier to a medium including a target compound, allowing microorganisms included in the biomass to be carried on the inorganic microparticles, and culturing while monitoring an abundance ratio of the target compound-degrading microorganism in microorganisms carried on the inorganic microparticle carrier; and a step of, after the abundance of the target compound-degrading microorganism reaches a predetermined value, collecting the inorganic microparticle carrier carrying the target compound-degrading microorganism to obtain the microbiologic agent.

The target compound according to the present embodiment is not particularly limited as long as it is a compound that is degraded by a microorganism, but a compound contained in the drainage is preferred. Examples of such compound include ammonia, nitrous acid, benzene, toluene, styrene, xylene, catechol, protocatechuic acid, protocatechualdehyde, 2-phenylbutyric acid, 2-isopropylphenylbutyric acid, (S)-2-(4-chlorophenyl)-3-methylbutanoic acid, benzoic acid, and benzaldehyde. Of these, ammonia or (S)-2-(4-chlorophenyl)-3-methylbutanoic acid, which is desired to be removed from drainage, is preferred.

The medium including the target compound is not particularly limited as long as it includes the target compound and can be used to culture the target compound-degrading microorganism. Such a medium may be a medium in which salts, pH, and the like are adjusted artificially or may be sewage or wastewater. From a point of view of acclimating the target compound-degrading microorganism, it is preferable that the concentration of the target compound included in the medium is set such that the initial concentration thereof is low and then the concentration thereof is gradually increased during the culture process. The initial concentration may be set for each target compound as appropriate.

The target compound-degrading microorganism is a microorganism that can degrade and use the target compound as a nutrition source. The target compound-degrading microorganism according to the present embodiment is selected as appropriate according to the selection of the target compound. If ammonia is selected as the target compound, then examples include nitrifying bacteria (such as ammonia-oxidizing bacteria such as *Nitrosomonas*, nitrous acid-oxidizing bacteria such as *Nitrobacter, Nitrospira*). If (S)-2-(4-chlorophenyl)-3-methylbutanoic acid is selected as the target compound, then examples include bacteria in the family Sphingomonadaceae.

Examples of the biomass including the target compound-degrading microorganisms include activated sludge, soil, and microflora such as biofilm and, from a point of view of widespread use in the industry for purification of sewage, activated sludge is preferred. Examples of the activated sludge include sewage sludge, activated sludge from industrial drainage treatment facilities, and sludge from night soil treatment facilities.

The inorganic microparticle carrier may be of a material that is a metal and an inorganic salt or oxide thereof, that contains carbon or is chemically classified as an inorganic matter, or that is a pure substance or a mixture that contains organic state carbon at a content of about 1% or less. Examples of the inorganic microparticle carrier include industrial products (including non-standard products, by-products, and waste articles) such as alumina (aluminum oxide) and hydroxyapatite (calcium phosphate hydroxide); incineration ash of organic waste materials such as activated sludge; and coal combustion residuals, which are ashes of thermal power generation or coke ovens.

As the inorganic microparticle carrier, coal combustion residuals are above all preferred from a point of view of being at low cost and obtainable by simple and easy operations, and allowing the expression of microorganism activities to appear in a short-term. Among the coal combustion residuals, clinker ash or fly ash is preferred and fly ash is more preferred since its median particle size is 100 μm or less without sieving, etc. As the inorganic microparticle carrier, clinker ash can be used as well as fly ash after adjusting median particle size by grinding. The composition of the clinker ash or fly ash is not particularly limited.

The median particle size of the inorganic microparticle carrier is preferably 1 μm to 100 μm, more preferably 4 μm to 75 μm, and further preferably, 13 μm to 25 μm. If the median particle size is in such a range, the biomass including the target compound-degrading microorganism and the inorganic microparticle carrier are easier to aggregate when mixed and a suitable amount of the biomass including the target compound-degrading microorganism tends to be easier to be carried on the inorganic microparticle carrier.

The specific gravity of the inorganic microparticle carrier is not particularly limited, but 1.2-3.5 is preferred.

The inorganic microparticle carrier may be agglutinated using any of various flocculants as needed for the purpose of improving yield in the early period of culture. Examples of the flocculant include nonionic, cationic, and anionic polymer flocculants.

As a culture method according to the present embodiment, any of the batch, semi-batch, fed-batch, and continuous techniques may be used. From a point of view of efficiently preparing the microorganism with slow proliferation and low yield of cells, for example, the continuous culture technique in which the concentration of the target compound supplied to a container for culturing the microorganism (hereinafter, also referred to as a reaction tank) is logarithmically increased over culture time may be used as a culture method, as described in Japanese Unexamined Patent Publication No. 119-187272.

In the present embodiment, the reaction tank is not particularly limited in its specification and culture tanks, activated sludge treatment tanks, and the like that have been used conventionally may be used. If the target compound-degrading microorganism is an aerobic microorganism, a reaction tank illustrated in FIG. 1, for example, may be used from a point of view of capability of accumulating the target compound-degrading microorganism at high densities and culturing efficiently with low operating cost and simple and easy operation management.

Figure 1:
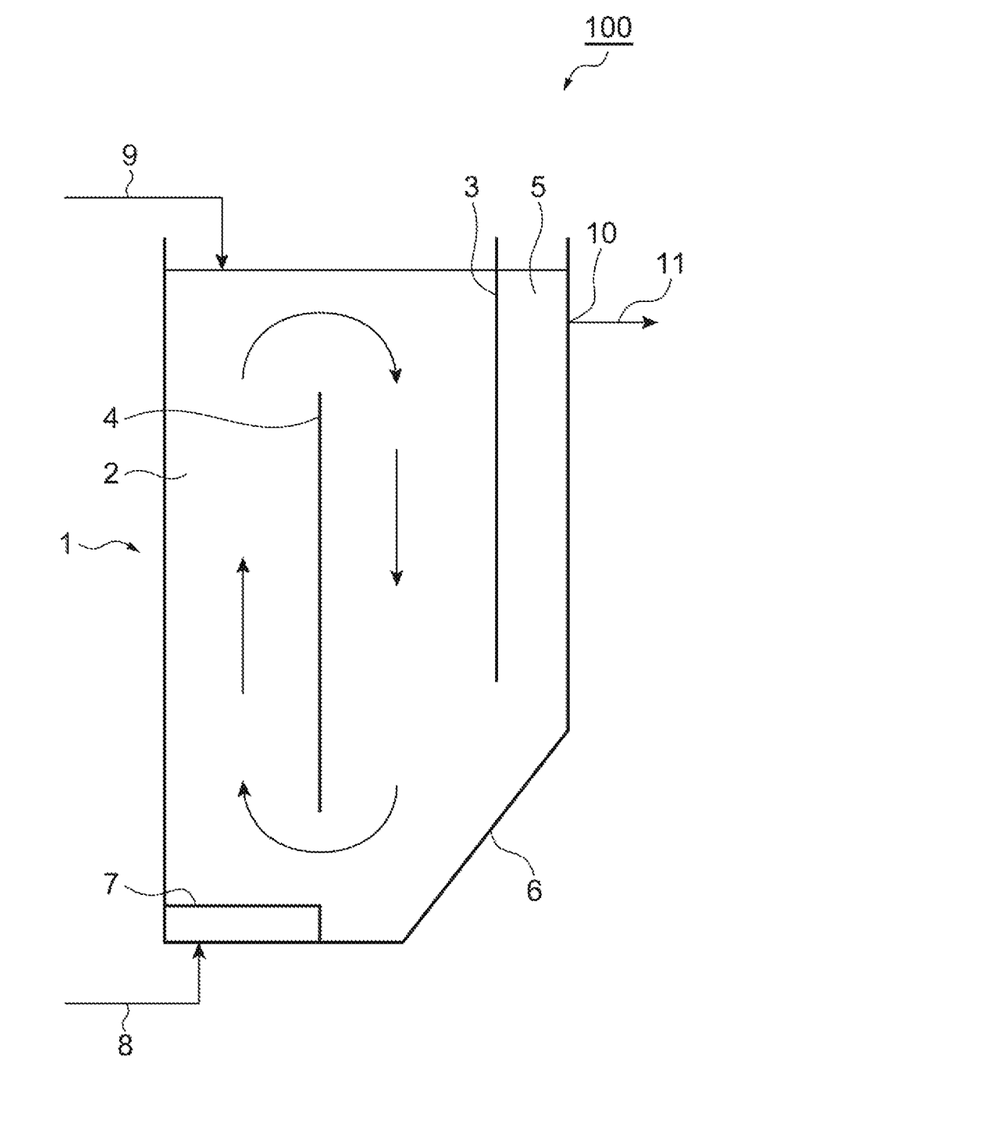
FIG. 1 is a schematic longitudinal section of a reaction tank for producing a microbiologic agent of the present embodiment.

The reaction tank 100 illustrated in FIG. 1 is constituted of a split-type bubble tower reactor. This reactor has a structure in which a partition 3 and a current plate 4 are incorporated in a culture tank 1 and divided by the partition 3 into an aeration part 2 and a sedimentation part 5. The bottom of the sedimentation part 5 is composed of a tapered slope 6 and solid bodies that have descended along the slope 6 ascend in the aeration part 2, one side of the division with the current plate 4, by an upwelling current with air or high oxygen partial pressure gas 8 flowed in from an aeration device 7, come in contact and mixed with inflow water 9 above the aeration part 2, descend in the sedimentation part 5, the other, outer, side of the division with the current plate 4, and reach the slope 6 at the bottom, forming a circulating flow.

Solid bodies and clear water are separated by gravity in the sedimentation part 5 and the solid bodies return to the aeration part 2 along the slope 6 and the clear water is drained as treated water 11 from an outlet 10. As the inflow water 9 that flows in from above the surface of water of the aeration part 2, a synthetic medium, drainage, or the like including the target compound is supplied and culture is conducted. The supply of the inflow water 9 may be continuous or intermittent.

In the reaction tank illustrated in FIG. 1, an inorganic microparticle carrier is allowed to flow in the reaction tank and microorganisms included in biomass are accumulated and carried on the carrier and cultured. In culture, a medium is supplied to the reaction tank, the air or high oxygen partial pressure gas 8 is supplied from the aeration device 7, an inorganic microparticle carrier is allowed to flow while circulating the medium including the inorganic microparticle carrier in the aeration part 2, and microorganisms are accumulated on the inorganic microparticle carrier. According to such a method, the high load operation is possible since it tends to be capable of accumulating the target compound-degrading microorganism at high densities and culturing efficiently with low operating cost and simple and easy operation management, and efficiency of use of oxygen supplied in the tank is high.

In the present embodiment, the kind of the target compound-degrading microorganism carried on the inorganic microparticle carrier and the abundance ratio thereof to the microorganisms carried on the inorganic microparticle carrier can be determined by a method described below. Therefore the change of the abundance ratio of the target compound-degrading microorganism can be examined by regularly examining the abundance ratio during the process of culturing the inorganic microparticle carrier carrying the target compound-degrading microorganism.

If the abundance ratio of the target compound-degrading microorganism on the inorganic microparticle carrier carrying the target compound-degrading microorganism reaches a predetermined value, then it can be judged to have a predetermined function as a microbiologic agent that degrades the target compound and therefore the inorganic microparticle carrier carrying the target compound-degrading microorganism can be collected to obtain a microbiologic agent according to the present embodiment. The abundance ratio of the target compound-degrading microorganism at which a microparticle carrier is judged to have a predetermined function as a microbiologic agent can be set as appropriate depending on the target compound. If ammonia is selected as the target compound, for example, the abundance ratio of the nitrifying bacterium is preferably 5% or more, more preferably 10% or more, and further preferably 15% or more. When (S)-2-(4-chlorophenyl)-3-methylbutanoic acid is selected as the target compound, for example, the abundance ratio of the (S)-2-(4-chlorophenyl)-3-methylbutanoic acid-degrading microorganism is preferably 5% or more, more preferably 6% or more, and further preferably 7% or more.

After the abundance ratio of the target compound-degrading microorganism reaches a predetermined value, the inorganic microparticle carrier carrying the target compound-degrading microorganism is collected, which is defined as a microbiologic agent according to the present invention. In the present embodiment, only the inorganic microparticle carrier carrying the target compound-degrading microorganism may be collected and defined as a microbiologic agent, the medium including the inorganic microparticle carrier carrying the target compound-degrading microorganism may be defined as a microbiologic agent, or what is remained after removing water by concentration or drying from the medium including the inorganic microparticle carrier carrying the target compound-degrading microorganism may be defined as a microbiologic agent. In preservation and storage of a microbiologic agent of the present embodiment, the agent may be treated with a high oxygen partial pressure gas beforehand if the carried microorganism is an aerobic microorganism.

In the method for production of the present embodiment, a microbiologic agent can be produced stably and efficiently since problems such as proliferation inhibition can be detected quickly and dealt with by examining the change of the abundance ratio of the target compound-degrading microorganism included in the microbiologic agent (the inorganic microparticle carrier carrying the target compound-degrading microorganism) in production by monitoring the target compound-degrading microorganism during the culture process. For example, if proliferation inhibition of the target compound-degrading microorganism is predicted, the proliferation of the target compound-degrading microorganism can be controlled appropriately by taking a measure such as regulating the amount of the target compound added.

<Calculation of Abundance Ratio of Target Compound-Degrading Microorganism>

The abundance ratio of the target compound-degrading microorganism is determined by a method comprising: a step of amplifying a predetermined region of a 16S rRNA gene of microorganisms carried on the inorganic microparticle carrier to obtain an amplified product; and a step of analyzing nucleotide sequence data of the amplified product, dividing the obtained nucleotide sequence data into a plurality of groups based on homologies among the nucleotide sequence data, considering that microorganisms having each group of nucleotide sequence data are of a single kind, determining the kind of the target compound-degrading microorganism based on representative nucleotide sequence data of respective groups, and calculating the abundance ratio of the target compound-degrading microorganism in all microorganisms based on the number of the obtained nucleotide sequence data.

As the 16S rRNA gene of the target compound-degrading microorganism, for example, DNA directly prepared from the inorganic microparticle carrier carrying the target compound-degrading microorganism may be used. As a method of preparing DNA, a method well-known by those skilled in the art may be used: for example, a commercially available DNA extraction kit may be used.

A predetermined region of the 16S rRNA gene included in the prepared DNA is amplified and the amplified product obtained is used in the following analysis. In the 16S rRNA gene, there are preserved regions containing common sequences between species on the gene and variable regions (V1-V9) containing sequences that vary depending on the species, the genus, or the like. It is preferred that the region to be amplified is a variable region flanked by preserved regions since 16S rRNA genes derived from a plurality of species of microorganisms can be obtained in a single amplification step and a plurality of kinds of microorganisms can be distinguished. Examples of the region to be amplified include ranges containing the V3-V4 region. The nucleotide number of the nucleotide sequence of the region to be amplified is preferably 100-1500 nucleotides, more preferably 300 to 800 nucleotides, and further preferably 400 to 600 nucleotides. If the region to be amplified has such a length, then the reliability of analysis tends to be sufficient to classify a plurality of kinds of microorganisms.

The method of amplifying the predetermined region in the 16S rRNA gene is not particularly limited but a method well-known to those skilled in the art may be used. Examples of such a method include polymerase chain reaction (PCR).

If PCR is used for the amplification, then it is preferred that primers to be used, for a forward primer and a reverse primer, are universal primers designed to hybridize to preserved regions flanking a variable region in the 16S rRNA gene under stringent conditions from a point of view of detecting a plurality of microorganisms included in the inorganic microparticle carrier carrying the target compound-degrading microorganism.

The forward and reverse primers have universal primer sequences that are nucleotide sequences that hybridize to preserved regions in the 16S rRNA gene under stringent conditions. The lengths of the universal primer sequences are preferably 15 to 40 nucleotides, more preferably 15 to 30 nucleotides, and further preferably 15 to 25 nucleotides.

As used herein, "stringent conditions" means conditions under which complementary strands of nucleotide strands having a homology with a target sequence preferentially hybridize to the target sequence and complementary strands of nucleotide strands that do not have such a homology do not substantially hybridize. Stringent conditions are sequence-dependent and vary in a variety of situations. Longer sequences specifically hybridize at higher temperatures. In general, stringent conditions are selected so that the temperature is about 5° C. lower than the thermal melting temperature (Tm) of the particular sequence at the prescribed ionic strength and pH. Tm is a temperature at which 50% of nucleotides complementary to the target sequence hybridize to the target sequence in equilibrium under the prescribed ionic strength, pH and DNA concentration.

Examples of the method for analyzing nucleotide sequences of amplified products include the sequence analysis with a sequencer. The sequencer is preferably a next-generation sequencer from a point of view of being capable of analyzing a plurality of species of microorganisms simultaneously and cyclopedically without separating amplified products (amplicons) obtained by amplification of a predetermined region in the 16S rRNA gene and examples include GS FLX+ System (manufactured by F. Hoffmann-La Roche Ltd.), and MiSeq (manufactured by Illumina, Inc.).

If GS FLX+ System (manufactured by F. Hoffmann-La Roche Ltd) is used as the sequencer, then the universal primers may have certain sequences other than the universal primer sequences. For example, the forward primer is designed to contain, from the 5' end to, an adapter sequence necessary for sequencing in the sequence analysis, a barcode sequence specific to each sample, and a universal primer sequence and the reverse primer is designed to contain, from the 5' end, an adapter sequence necessary for sequencing in the sequence analysis and a universal primer sequence. Barcode sequences are used to distinguish samples and arbitrarily designed nucleotide sequences that correspond to the number of the samples to be simultaneously analyzed with a sequencer. A large number of samples can be analyzed by one sequence analysis by using primers having such barcode sequences. Adapter sequences and barcode sequences that designated by the manufacturer may be used. The length of the barcode sequences may be designed according to the number of samples to be used in the nucleotide sequence analysis and, for example, 8 to 15 nucleotides.

A method of analyzing nucleotide sequence data obtained by GS FLX+ System is described below, but the present invention is not limited to this.

Sequences of the nucleotide sequence data obtained by the sequence analysis are assigned to their specific samples based on sample-specific barcode sequences included in the nucleotide sequence data. Assigned nucleotide sequence data is further sorted by the sequence lengths of the nucleotide sequence data, the number of nucleotides that are mismatched with the universal primer sequence, mean quality values of the sequenced nucleotide sequence data calculated by a quality program provided with the sequencer, and the like and highly accurate nucleotide sequence data is obtained.

Obtained highly accurate nucleotide sequence data is divided into a plurality of groups based on homologies in the nucleotide sequence data by OTU (Operational Taxonomic Unit) analysis. The homologies in nucleotide sequence data in the same group may be set according to the required reliability and may be 95% or more, 97% or more, or 99% or more. Examples of software for conducting the OTU analysis include Uclust (http://drive5.com/usearch/manual/uclust_algo.html), UPARSE (http://drive5.com/usearch/manual/uparse_pipeline.html), and USEARCH (http://www.drive5.com/usearch).

In a result of the OTU analysis, microorganisms having nucleotide sequence data in the same group are a single kind of microorganisms. "Kind" as used herein include the family, the genus, and the species in the taxonomy. Representative nucleotide sequence data for each group is searched by homology search of a database such as DDBJ, GenBank, RDP, or Greengenes and a microorganism having nucleotide sequence data having the highest homology is identified as a microorganism having the representative nucleotide sequence data. The kind of the group of microorganisms that includes the representative nucleotide sequence data determined can be thereby identified. If the kinds of the groups of microorganisms are identified, it can be determined which group of microorganisms are target compound-degrading microorganisms based on the information such as a database. As used herein, the representative nucleotide sequence data refers to nucleotide sequence data having a homology equal to or higher than a threshold with any of nucleotide sequence data in each group.

In a result of the OTU analysis, the number of groups can be considered to be same as the number of kinds of microorganisms constituting the microbial flora within the detectable range. From the number of sequences in the nucleotide sequence data in each group, a ratio to the number of sequences in the whole nucleotide sequence data obtained, that is, the abundance ratio of the microorganism species of the group among the whole microbial flora can be determined. By determining the group of the target compound-degrading microorganism from the representative nucleotide sequence data by the method described above, the abundance ratio can be calculated.

<Method for Degrading Compound>

Microbiologic agents of the present embodiment may be used to degrade the target compound. Examples of methods for degrading the target compound include methods involving adding a microbiologic agent of the present embodiment to a waste fluid, etc. containing the target compound and stirring the mixture. In such a method, the amount of the microbiologic agent to be added may be set as appropriate depending on the kind of the target compound, the volume of the reaction tank, the abundance ratio of the target compound-degrading microorganism carried on the microbiologic agent, and the like.

<Method for Evaluating Microbiologic Agent>

A method for evaluating a microbiologic agent of the present embodiment comprises a step of evaluating a microbiologic agent using an abundance ratio of a target compound-degrading microorganism as an indicator. The abundance ratio of the target compound-degrading microorganism can be determined using the method described above.

Examples of the microbiologic agent used in the method of evaluation of the present embodiment include a microbiologic agent stored after the production.

The evaluation of the microbiologic agent is performed by calculating the abundance ratio of the target compound-degrading microorganism to the microorganisms included in the microbiologic agent. In the method of evaluation, for example, the abundance ratios of the target compound-degrading microorganism included in the microbiologic agent just after the production and in the microbiologic agent in storage are compared and the degradation activity of the microbiologic agent in storage may be judged to be decreased if the abundance ratio of the target compound-degrading microorganism included in the microbiologic agent in storage is decreased.

EXAMPLES

Example 1

(Material)

Concentrates of components to be used in the production of a medium was prepared by a method described below. 35.4 g of $(NH_4)_2SO_4$ and 7.7 g of $Na_2HPO_4$ were dissolved in 500 mL of pure water to obtain a nitrogen phosphorus solution containing 15000 mg/L of ammonia nitrogen. 110 g of KCl, 50 g of $CaCl_2.2H_2O$ and 1 mg of $CoCl_2$ were dissolved in 1000 mL of pure water to obtain Inorganic salt solution 1. 5 mg of $NaMoO_4.2H_2O$ was dissolved in 1000 mL of pure water to obtain Inorganic salt solution 2. 85 g $MgSO_4.7H_2O$, 8.5 g of $FeSO_4.7H_2O$, 2 g of $MnSO_4.5H_2O$, 100 mg of $ZnSO_4$, and 100 mg of $CuSO_4.5H_2O$ were dissolved in 1000 mL of pure water to obtain Inorganic salt solution 3. The medium to be supplied during culture was produced by dissolving 0.2 g of $(NH_4)_2SO_4$ and 1.54 g of $Na_2HPO_4$ in 1000 mL of pure water and adding 1 ml of Inorganic salt solution 1, 1 ml of Inorganic salt solution 2, and 1 mL of Inorganic salt solution 3. An amount required of the medium was produced as needed for continuous supply during the culture period. Activated sludge suspensions were prepared by collecting activated sludge from an aeration tank in a chemical factory and adjusting the activated sludge concentration to 5000 mg-MLSS/L with pure water. MLSS refers to mixed liquor volatile suspended solids. MLSS was measured according to the method described in "Method of Sewage Testing," first volume, 2012, Japan Sewage Works Association. A dispersion liquid of an inorganic microparticle carrier was produced by mixing a suspension obtained by adding 500 g of fly ash to 800 ml of pure water and mixing and a liquid obtained by dissolving 60 g of SUMIFLOC FA-40H (manufactured by MT AquaPolymer Inc.) in 600 ml of pure water.

(Production of Microbiologic Agent)

Microbiologic agents were produced using an airlift continuous reaction tank with an aeration part and a sedimentation part for conducting the solid-liquid separation, 10 L of the activated sludge suspension. 10 mL of the nitrogen phosphorus solution, 10 ml of Inorganic salt solution 1, 10 ml of Inorganic salt solution 2, 10 mL of inorganic salt solution 3, and 1.4 L of the dispersion liquid of the inorganic microparticle carrier were added to the reaction tank and the mixture was stirred by airlift to conduct the culture. pH of the medium obtained by mixing these was controlled to be near 7.5 with a 10% by mass solution of $H_3PO_4$ and a 10% by mass solution of $Na_2CO_3$. The water temperature was controlled to be 25° C. The medium in the reaction tank is hereinafter referred to as the culture liquid.

After the onset of culture, the concentration of the ammonia nitrogen in a culture liquid was measured and the supply of the medium for supply was started when the ammonia nitrogen was exhausted. The ammonia nitrogen concentration in the culture liquid and the flow rate of the medium were adjusted so as to prevent the proliferation inhibition of the nitrifying bacterium depending on the results of the measurement of the ammonia concentration, the nitrous acid concentration, the nitric acid concentration, and the abundance ratio of the nitrifying bacterium in the culture liquid and so as to gradually increase the ammonia nitrogen concentration in the culture liquid.

The culture liquid on Day 36 of the culture was collected from the aeration part of the reaction tank and this was defined as a microbiologic agent in which the nitrifying bacterium was densified.

(Measurement of Ammonia Nitrogen)

A culture liquid from which activated sludge had been separated by sedimentation was collected from the sedimentation part of the reaction tank, this was filtered through a syringe filter (manufactured by Advantec Toyo Kaisha, Ltd.) having a pore size of 0.45 μm and a diameter of 25 mm, and measured using an ammonia nitrogen detection kit and the spectrophotometer Spectroquant NOVA60 (manufactured by Merck Millipore Corporation).

(Calculation of Removal Rate of Ammonia Nitrogen)

From the ammonia nitrogen concentration contained in the culture liquid at the time of collecting the culture liquid from which activated sludge was separated by sedimentation from the sedimentation part of reaction tank and the ammonia nitrogen concentration contained in the medium for supply, the removal rate of ammonia nitrogen was calculated.

$$\text{removal rate of ammonia nitrogen (\%)} = \left[1 - \frac{\text{ammonia nitrogen concentration in culture liquid (mg-N/L)}}{\text{ammonia nitrogen concentration in medium for supply (mg-N/L)}}\right] \times 100 \quad \text{[Expression 1]}$$

(Calculation of Capacity of Nitrogen Treatment)

From the ammonia nitrogen concentration contained in the medium at the time of collecting the culture liquid from which activated sludge was separated by sedimentation from the sedimentation part of reaction tank, the ammonia nitrogen concentration contained in the medium for supply, the flow of the medium for supply, and the volume of the culture liquid in the aeration part of the reaction tank, the capacity of nitrogen treatment was calculated.

$$\text{capacity of nitrogen treatment (mg-N/L·hr)} = \frac{\text{ammonia nitrogen concentration in medium for supply (mg-N/L)} - \text{ammonia nitrogen concentration in culture liquid (mg-N/L)}}{\text{volume of culture liquid in aeration part of reaction tank (mL)/flow of medium for supply (mL/min)/60 min}} \quad \text{[Expression 2]}$$

(Determination of Kind of Microorganism and Calculation of Abundance Ratio of Each Microorganism)

Preparation of DNA

The detection of a nitrifying bacterium and the calculation of its abundance ratio was conducted by collecting an inorganic microparticle carrier carrying a target compound-degrading microorganism, in which activated sludge was adhered to an inorganic microparticle carrier in culture and analyzing nucleotide sequence data of the 16S rRNA gene of the microorganisms included in the carrier. DNA of the microorganisms in the inorganic microparticle carrier carrying the target compound-degrading microorganism was prepared by the following methods.

1.5 mL of the medium containing the inorganic microparticle carrier carrying the target compound-degrading microorganism was collected and centrifuged (13000 rpm, 5 minutes) at room temperature. After the removal of the supernatant, 1 mL of sterilized physiological saline was added, mixed by inversion for approximately 5 seconds, and centrifuged (13000 rpm, 5 minutes) at room temperature. After the removal of the supernatant, 300 μL of Lysis buffer (manufactured by AMR Inc.) was added and mixed well. After the addition of this suspension into a tube including beads (Easy Extract for DNA (manufactured by AMR Inc.)), the suspension was subjected to the lysis with stirring with a vortex mixer for 2 minutes. 300 μL of a TE solution (10 mM Tris, 1 mM EDTA, pH 8.0; hereinafter, referred to as the TE solution) was added to the lysate and the mixture was centrifuged (13000 rpm, 5 minutes) at 4° C. 450 μL of the supernatant was subsequently transferred into a new tube, 600 μL of phenol-mixed solution (one provided for Easy Extract for DNA (manufactured by AMR Inc.)) was added to this, stirred with a vortex mixer for 1 minute, and then centrifuged (13000 rpm, 5 minutes) at 4° C. 300 μL of the supernatant was collected and transferred into a new tube (1.5 mL), 1200 μL of ethanol (99.5%) was added to this, which was centrifuged (13000 rpm, 5 minutes) at 4° C. After the removal of the supernatant, 1000 μL of cold ethanol (70%) was added to the tube and centrifuged (13000 rpm, 5 minutes) at 4° C., and the obtained DNA pellet was vacuum dried. 150 μL of the TE solution was added to the dried DNA pellet to obtain a DNA solution of the microorganisms in the inorganic microparticle carrier carrying the target compound-degrading microorganism.

Amplification of 16S rRNA Gene

The concentration of double-stranded DNA in the prepared DNA solution was measured, and using 50 ng of DNA calculated based on the measurement as a template and a universal primer set (a forward primer and a reverse primer), the V3-V4 region of the 16S rRNA gene was amplified by PCR. For the PCR, 50 µL of a reaction solution containing 50 pmol each of the primers was prepared using "Premix Ex Taq Hot Start Version" (registered trademark) manufactured by Takara Bio Inc., 2 minutes of pre-heating at 94° C. was conducted, and then denaturation, annealing, and extension respectively at 98° C.×10 seconds, 50° C.×30 seconds, and 72° C.×80 seconds were repeated 25 cycles. By the PCR using the universal primer set, DNA fragments (about 570 bp) of various microorganisms included in the inorganic microparticle carrier carrying the target compound-degrading microorganism were amplified.

A primer having, from the 5' end, Adapter A sequence consisting of the nucleotide sequence set forth in SEQ ID NO: 1, a barcode sequence consisting of 10 nucleotides, and a universal primer sequence consisting of the nucleotide sequence set forth in SEQ ID NO: 2 was used as a forward primer. A primer having, from the 5' end, Adapter B sequence consisting of the nucleotide sequences set forth in SEQ ID NO: 3 and a universal primer sequence consisting of the nucleotide sequence set forth in SEQ ID NO: 4 was used as a reverse primer.

Sequence Analysis

The amplified PCR product was treated with a DNA cleaner (manufactured by Wako Pure Chemical Industries, Ltd.) and the DNA was purified. The purified DNA was eluted and collected with 200 µL of the TE solution. The purified DNA solution collected was subjected to agarose gel electrophoresis and a band detected at the position of about 570 bp was cut out with gel. The DNA was extracted from the gel cut out using MinElute Gel Extraction Kit (manufactured by Qiagen) to obtain a sample for sequencing with a sequencer.

The sample for sequencing was applied to a GS FLX+ System sequencer (manufactured by F. Hoffmann-La Roche Ltd.) and the sequence analysis was conducted. Conditions, procedure, etc. for the sequence were according to the protocol prescribed by the manufacturer. The data of each nucleotide sequence obtained was assigned to the sample specific to the nucleotide sequence data based on the sample-specific barcode sequence contained in each nucleotide sequence data. Highly accurate nucleotide sequence data was then extracted by removing sequence data of sequences having a sequence length of less than 200 nucleotides or 1000 nucleotides or more, those having 1 or more nucleotides of mismatch with the universal primer sequence (the forward primer), and those for which a mean quality value determined using the quality program provided with the sequencer is 25 or less for the sequenced nucleotide sequence data.

OTU Analysis

The highly accurate nucleotide sequence data was subjected to the OTU analysis. In the OTU analysis, sequences having a homology of 95% or more to one another were classified in the same group and a plurality of groups were formed. The OTU analysis was conducted using Uclust. From information obtained by the OTU analysis, the determination of the kinds of the microorganisms included in the inorganic microparticle carrier carrying the target compound-degrading microorganism and the calculation of the abundance ratios of the microorganisms were conducted.

(Result)

Summary of the removal rate of ammonia nitrogen, the capacity of nitrogen treatment, and the abundance ratios of nitrifying bacteria (ammonia-oxidizing bacterium (*Nitrosomonas*) and nitrous acid-oxidizing bacteria (*Nitrobacter* and *Nitrospira*)) included in the inorganic microparticle carrier carrying the target compound-degrading microorganism after the indicated days of culturing of the inorganic microparticle carrier carrying the target compound-degrading microorganism is illustrated in Table 1. With the gene analysis information of the microorganisms included in the inorganic microparticle carrier carrying the target compound-degrading microorganism in culture, the change of the abundance ratios of the nitrifying bacteria included in the inorganic microparticle carrier carrying the target compound-degrading microorganism could be measured over time. Moreover, it was demonstrated that, with the increase in various nitrifying bacteria, the capacity of nitrogen treatment of the inorganic microparticle carrier carrying the target compound-degrading microorganism was increased.

TABLE 1

| Days of culturing (days) | Removal rate of ammonia nitrogen (%) | Capacity of nitrogen treatment (mg-N/L · hr) | Abundance ratio of microorganism (%) | | |
|---|---|---|---|---|---|
| | | | Nitrosomonas | Nitrobacter | Nitrospira |
| 0 | — | — | <0.1 | 0.3 | <0.1 |
| 8 | 81.8 | 3.9 | <0.1 | 0.4 | 0.2 |
| 15 | 99.6 | 11.3 | <0.1 | 0.1 | 0.6 |
| 29 | 100 | 30.4 | 18.9 | 5.9 | 6.9 |
| 36 | 100 | 42.8 | 26.8 | 8.2 | 5.6 |

Example 2

(Material)

Concentrates of components to be used in the production of a medium was prepared by a method described below. 100 g of $MgSO_4 \cdot 7H_2O$ was dissolved in 1000 mL of pure water to obtain Inorganic salt solution A. 4.152 g of $Na_2HPO_4$, 2.244 g of $NaH_2PO_4$, and 1.2 g of $(NH_4)_2SO_4$ were dissolved in 300 mL of pure water to obtain Inorganic salt solution B. A (S)-2-(4-chlorophenyl)-3-methylbutanoic acid solution (10 g/L) obtained by dissolving 1.18 g of (S)-2-(4-chlorophenyl)-3-methylbutanoic acid (with a purity of about 85% by mass) in 100 mL of pure water was used. A dispersion liquid of an inorganic microparticle carrier was prepared by adding, mixing, and suspending 50 g of incineration ash of activated sludge to 250 ml of pure water. An activated sludge suspension obtained by collecting activated sludge from an aeration tank of a chemical factory was used as it is. The medium to be supplied during culture was produced by dissolving 1.0 g of $(NH_4)_2SO_4$, 1.3 g of $Na_2HPO_4$, and 0.9 g of $NaH_2PO_4$ in 1000 mL, of pure water and adding 4.0 mL of the (S)-2-(4-chlorophenyl)-3-methylbutanoic acid solution, 1 ml of Inorganic salt solution 1, 1 ml of Inorganic salt solution 2, and 1 mL of Inorganic salt solution 3. An amount required of the medium was produced as needed for continuous supply during the culture period. In addition, a factory-derived byproduct oil containing methanol and water at the ratio of about 7:3 (v/v) was used as a carbon source to be used at the onset of culture.

(Production of Microbiologic Agent)

Microbiologic agents were produced using an airlift continuous reaction tank with an aeration part (with a volume of 1 L) and a sedimentation part (with a volume of 0.4 L). A medium was prepared by adding 570 mL of the activated sludge suspension, 4.9 mL of Inorganic salt solution A, 300 mL of Inorganic salt solution B, 13.2 µL of the factory-derived byproduct oil, 9.876 mL of the (S)-2-(4-chlorophenyl)-3-methylbutanoic acid solution, 250 mL of the dispersion liquid of the inorganic microparticle carrier, and 70 mL of pure water to the reaction tank. This medium was stirred by airlift and cultured. pH of the medium was controlled to be near 6.9 using a 10% by mass solution of $Na_2CO_3$. The water temperature was controlled to be 25° C. The medium in the reaction tank is hereinafter referred to as the culture liquid.

After the onset of culture, the (S)-2-(4-chlorophenyl)-3-methylbutanoic acid concentration in the culture liquid was measured and continuous culture was conducted by continually supplying the medium containing the predetermined concentration of (S)-2-(4-chlorophenyl)-3-methylbutanoic acid if a marked decrease in concentration of (S)-2-(4-chlorophenyl)-3-methylbutanoic acid was found. Salts contained in the medium to be added were increased depending on the amount of (S)-2-(4-chlorophenyl)-3-methylbutanoic acid to be added. To see the change of microorganisms included in the inorganic microparticle carrier carrying the target compound-degrading microorganism in culture, DNA extraction from the microorganisms included in the inorganic microparticle carrier carrying the target compound-degrading microorganism in culture was conducted as needed.

Measurement of
(S)-2-(4-chlorophenyl)-3-methylbutanoic Acid
Concentration

The (S)-2-(4-chlorophenyl)-3-methylbutanoic acid concentration in the medium was calculated by subjecting the medium to HPLC under the following conditions.
Apparatus: LC-10A (manufactured by Shimadzu Corporation)
Column: SUMIPAX ODS A-211 4.6 mm×250 mm, 5µ (manufactured by Sumika Chemical Analysis Service Ltd.)
Solvent: Solution A a 0.01% TFA aqueous solution, Solution B acetonitrile, Solution A:Solution B=4:6
Flow rate: 1.0 mL/min
Oven temperature: 40° C.
Detector: UV 220 nm
Sample injection volume: 10 µL Calculation of Removal Rate of
(S)-2-(4-chlorophenyl)-3-methylbutanoic Acid The removal rate of (S)-2-(4-chlorophenyl)-3-methylbutanoic acid was calculated from the (S)-2-(4-chlorophenyl)-3-methylbutanoic acid concentration included in the culture liquid at the time of collecting the culture liquid from which activated sludge was separated by sedimentation from the sedimentation part of reaction tank and the (S)-2-(4-chlorophenyl)-3-methylbutanoic acid concentration included in the medium for supply.

$$\text{removal rate of } (S)\text{-2-(4-chlorophenyl)-3-methylbutanoic acid } (\%) = \left[1 - \frac{(S)\text{-2-(4-chlorophenyl)-3-methylbutanoic acid concentration in culture liquid (mg/L)}}{(S)\text{-2-(4-chlorophenyl)-3-methylbutanoic acid concentration in medium for supply (mg/L)}}\right] \times 100$$ [Expression 3]

Calculation of Capacity of
(S)-2-(4-chlorophenyl)-3-methylbutanoic Acid
Treatment The capacity of (S)-2-(4-chlorophenyl)-3-methylbutanoic acid treatment was calculated from the (S)-2-(4-chlorophenyl)-3-methylbutanoic acid concentration included in the medium at the time of collecting the culture liquid from which activated sludge was separated by sedimentation from the sedimentation part of reaction tank, the (S)-2-(4-chlorophenyl)-3-methylbutanoic acid concentration included in the medium for supply, the flow of the medium for supply, and the volume of culture liquid of the aeration part in the reaction tank.

$$\text{capacity of } (S)\text{-2-(4-chlorophenyl)-3-methylbutanoic acid treatment (mg/L} \cdot \text{hr)} = \frac{(S)\text{-2-(4-chlorophenyl)-3-methylbutanoic acid concentration in medium for supply (mg/L)} - (S)\text{-2-(4-chlorophenyl)-3-methylbutanoic acid concentration in culture liquid (mg/L)}}{\text{volume of culture liquid in aeration part of reaction tank (mL)} / \text{flow of medium for supply (mL/min)} / 60 \text{ min}}$$ [Expression 4]

(Determination of Kind of Microorganism and Calculation of Abundance Ratio of Each Microorganism)

The detection of the (S)-2-(4-chlorophenyl)-3-methylbutanoic acid degradation microbe and the calculation of its abundance ratio were conducted by collecting the inorganic microparticle carrier carrying the target compound-degrading microorganism, in which activated sludge was adhered to the inorganic microparticle carrier in culture and analyzing the gene analysis information using its DNA. The gene analysis information of the microorganism in the inorganic microparticle carrier carrying the target compound-degrading microorganism was obtained by a method similar to that in Example 1.

(Result)

Summary of the removing rate of (S)-2-(4-chlorophenyl)-3-methylbutanoic acid, the capacity of (S)-2-(4-chlorophenyl)-3-methylbutanoic acid treatment, and the abundance ratio of the (S)-2-(4-chlorophenyl)-3-methylbutanoic acid-degrading microbe (Sphingomonadaceae) included in the inorganic microparticle carrier carrying the target compound-degrading microorganism after the indicated days of culturing of the inorganic microparticle carrier carrying the target compound-degrading microorganism is illustrated in Table 2. With the gene analysis information of the microorganisms included in the inorganic microparticle carrier carrying the target compound-degrading microorganism in culture, the change in the abundance ratio of the (S)-2-(4-chlorophenyl)-3-methylbutanoic acid-degrading microbe could be measured over time. Moreover, it was demonstrated that, with the increase in Sphingomonadaceae bacteria, the capacity of (S)-2-(4-chlorophenyl)-3-methylbutanoic acid treatment of the inorganic microparticle carrier carrying the target compound-degrading microorganism was increased.

TABLE 2

| Days of culturing (days) | Removal rate of (S)-2-(4-chlorophenyl)-3-methylbutanoic acid (%) | Capacity of (S)-2-(4-chlorophenyl)-3-methylbutanoic acid treatment (mg/L · hr) | Abundance ratio of microorganism (%) Sphingomonadaceae |
|---|---|---|---|
| 0 | — | — | 0.1 |
| 9 | 100 | 3.7 | 11.3 |
| 27 | 100 | 1.3 | 9.8 |
| 41 | 100 | 7.8 | 12.4 |

Example 3

As inorganic salt solutions to be used in the production of a medium, Inorganic salt solution 1, Inorganic salt solution 2, and Inorganic salt solution 3 same as those in Example 1 were used. The (S)-2-(4-chlorophenyl)-3-methylbutanoic acid solution same as that in Example 2 was used. The inflow water was produced by dissolving 1 mL of the (S)-2-(4-chlorophenyl)-3-methylbutanoic acid solution, 1 g of $(NH4)_2SO_4$, 1.298 g of $Na_2HPO_4$, 0.912 g of $NaH_2PO_4$ in 1000 mL of pure water and adding 1 ml of Inorganic salt solution 1, 1 ml of Inorganic salt solution 2, and 1 mL of Inorganic salt solution 3. An amount required of the inflow water was produced as needed for continuous supply during the (S)-2-(4-chlorophenyl)-3-methylbutanoic acid removal reaction period. An activated sludge suspension obtained by collecting activated sludge from an aeration tank of a chemical factory was used as it is.

((S)-2-(4-chlorophenyl)-3-methylbutanoic Acid Removal Reaction

The (S)-2-(4-chlorophenyl)-3-methylbutanoic acid removal reaction was conducted using an airlift continuous reaction tank with an aeration part (with a volume of 3 L) and a sedimentation part (with a volume of 1 L). The (S)-2-(4-chlorophenyl)-3-methylbutanoic acid removal reaction was conducted under 2 series of conditions: conditions (Series A) with no (S)-2-(4-chlorophenyl)-3-methylbutanoic acid-degrading microbiologic agent and conditions (Series B) with an (S)-2-(4-chlorophenyl)-3-methylbutanoic acid-degrading microbiologic agent. To the reaction tank, the inflow water was added and the activated sludge suspension was added and the activated sludge concentration was adjusted to 2408 mg-MLSS/L to obtain a culture liquid. MLSS refers to mixed liquor volatile suspended solids. Only to Series B, 459 mL of the (S)-2-(4-chlorophenyl)-3-methylbutanoic acid-degrading microbiologic agent on Day 54 after culture produced by removing the supernatant by centrifugation in Example 2 was added to obtain a culture liquid. The reactions were started by stirring the culture liquids of Series A and Series B. The inflow water was added at a speed of 1 mL/min. pH of the inflow water was controlled to near 7 using a 10% by mass solution of $Na_2CO_3$. The water temperature was controlled to be 25° C. The gene analysis information of the microorganisms in the microbiologic agent was obtained by a method similar to that in Example 1.

The measurement of the removal rate of (S)-2-(4-chlorophenyl)-3-methylbutanoic acid and the (S)-2-(4-chlorophenyl)-3-methylbutanoic acid-degrading microorganism was conducted by a method similar to that described in Example 2.

(Result)

Summary of the removal rate of (S)-2-(4-chlorophenyl)-3-methylbutanoic acid from the inflow water and the ratio of the (S)-2-(4-chlorophenyl)-3-methylbutanoic acid-degrading microorganism in Series A and Series B is illustrated in Table 3. In Series B, the ratio of the (S)-2-(4-chlorophenyl)-3-methylbutanoic acid-degrading microorganism was high and the removal rate of (S)-2-(4-chlorophenyl)-3-methylbutanoic acid was also high from Day 4.6 since the (S)-2-(4-chlorophenyl)-3-methylbutanoic acid-degrading microbiologic agent was added from the onset of the reaction. In Series A; on the other hand, increase in the ratio of the (S)-2-(4-chlorophenyl)-3-methylbutanoic acid-degrading microorganism was slow and the removal rate of (S)-2-(4-chlorophenyl)-3-methylbutanoic acid was also low in comparison with Series B,

TABLE 3

| | Series A (with no microbiologic agent) | | Series B (with microbiologic agent) | |
|---|---|---|---|---|
| Days of culturing (days) | Removal rate of (S)-2-(4-chlorophenyl)-3-methylbutanoic acid (%) | Abundance ratio of microorganism (%) Sphingomonadaceae | Removal rate of (S)-2-(4-chlorophenyl)-3-methylbutanoic acid (%) | Abundance ratio of microorganism (%) Sphingomonadaceae |
| 4.6 | 15.3 | 0.3 | 100 | 8.4 |
| 5.6 | 24.2 | 3.2 | 100 | 9.1 |
| 6 | 60.9 | 8.6 | 100 | 7.8 |
| 6.6 | 90.2 | 9.7 | 100 | 7.7 |

REFERENCE SIGNS LIST

1 . . . Culture tank, 2 . . . Aeration part, 3 . . . Partition, 4 . . . Current plate, 5 . . . Sedimentation part, 6 . . . Slope, 7 . . . Aeration device, 8 . . . Air or high oxygen partial pressure gas, 9 . . . Inflow water, 10 . . . Outlet, 11 . . . Treated water, 100 . . . Reaction tank.

The invention claimed is:

1. A method for producing a microbiologic agent comprising a target compound-degrading microorganism, comprising:
   (a) combining (i) biomass containing the target compound-degrading microorganism and (ii) an inorganic microparticle carrier in a medium containing a target compound to cause microorganisms contained in the biomass to be supported by the inorganic microparticles,
   (b) culturing the combination of (a),
   (c) during the culturing of (b), monitoring an abundance ratio of the target compound-degrading microorganism to all microorganisms supported by the inorganic microparticle carrier; and
   (d) examining the change of abundance ratio of the target compound-degrading microorganism supported by the inorganic microparticle carrier monitored in (c) and regulating the amount of the target compound to be added to the medium to prevent proliferation inhibition of the target compound-degrading microorganism, and
   (e) after the abundance ratio of the target compound-degrading microorganism monitored in (c) reaches a predetermined value, collecting the inorganic microparticle carrier that supports the target compound-degrading microorganism to obtain the microbiologic agent, wherein a predetermined value is an abundance ratio of the target compound-degrading microorganism to all microorganisms supported by the inorganic microparticle carrier at which the inorganic microparticle carrier is judged to have a predetermined function as a microbiologic agent that degrades the target compound;
   wherein the abundance ratio of the target compound-degrading microorganism is determined by a method comprising:

amplifying a predetermined region of a 16S rRNA gene of microorganisms supported by the inorganic microparticle carrier to obtain an amplified product; and analyzing nucleotide sequence data of the amplified product, dividing the obtained nucleotide sequence data into a plurality of groups based on homologies among the nucleotide sequence data, considering that microorganisms having each group of nucleotide sequence data are of a single kind, determining the kind of the target compound-degrading microorganism based on representative nucleotide sequence data of respective groups, and calculating the abundance ratio of the target compound-degrading microorganism to all microorganisms based on the number of the obtained nucleotide sequence data.

2. The method for production according to claim 1, wherein the target compound is (S)-2-(4-chlorophenyl)-3-methylbutanoic acid.

3. The method for production according to claim 1, wherein the target compound is ammonia.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: synthetic

<400> SEQUENCE: 1
ccatctcatc cctgcgtgtc tccgactcag                                         30

<210> SEQ ID NO 2
<211> LENGTH: 17
<212> TYPE: DNA
<213> ORGANISM: Artificial Sequence
<220> FEATURE:
<223> OTHER INFORMATION: synthetic

<400> SEQUENCE: 2
cctacgggag gcagcag                                                       17

<210> SEQ ID NO 3
<211> LENGTH: 30
<212> TYPE: DNA
<213> ORGANISM: Artificial Sequence
<220> FEATURE:
<223> OTHER INFORMATION: synthetic

<400> SEQUENCE: 3
cctatcccct gtgtgccttg gcagtctcag                                         30

<210> SEQ ID NO 4
<211> LENGTH: 21
<212> TYPE: DNA
<213> ORGANISM: Artificial Sequence
<220> FEATURE:
<223> OTHER INFORMATION: synthetic

<400> SEQUENCE: 4
ccgtcaattc cttttragtt t                                                  21
```